US00PP35434P3

(12) United States Plant Patent
Mazzardis

(10) Patent No.: US PP35,434 P3
(45) Date of Patent: Oct. 24, 2023

(54) BLUEBERRY PLANT NAMED 'NS 16-6'

(50) Latin Name: ***Vaccinium* hybrid**
Varietal Denomination: NS 16-6

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 18/084,500

(22) Filed: Dec. 19, 2022

(65) Prior Publication Data

US 2023/0270031 P1 Aug. 24, 2023

(30) Foreign Application Priority Data

Jan. 18, 2022 (QZ) ..... PBR 2022/0160

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

| | | | |
|---|---|---|---|
| PP25,858 | P3 | 9/2015 | Mazzardis |
| PP25,859 | P3 | 9/2015 | Mazzardis |
| PP25,860 | P3 | 9/2015 | Mazzardis |
| PP25,889 | P3 | 9/2015 | Mazzardis |
| PP26,172 | P3 | 12/2015 | Mazzardis |
| PP26,173 | P3 | 12/2015 | Mazzardis |
| PP27,142 | P3 | 9/2016 | Mazzardis |
| PP28,149 | P3 | 7/2017 | Mazzardis |
| PP28,217 | P3 | 7/2017 | Mazzardis |
| PP28,334 | P3 | 8/2017 | Mazzardis |
| PP28,357 | P3 | 9/2017 | Mazzardis |
| PP28,358 | P3 | 9/2017 | Mazzardis |
| PP30,626 | P3 | 7/2019 | Mazzardis |
| PP30,755 | P3 | 7/2019 | Mazzardis |
| PP30,756 | P3 | 7/2019 | Mazzardis |
| PP30,846 | P2 | 8/2019 | Mazzardis |
| PP30,934 | P3 | 10/2019 | Mazzardis |
| PP32,745 | P3 | 1/2021 | Mazzardis |
| PP32,781 | P3 | 2/2021 | Mazzardis |
| PP32,823 | P3 | 2/2021 | Mazzardis |
| PP32,897 | P3 | 3/2021 | Mazzardis |
| PP33,087 | P3 | 5/2021 | Mazzardis |
| PP33,154 | P3 | 5/2021 | Mazzardis |
| PP33,112 | P3 | 6/2021 | Mazzardis |
| PP33,137 | P3 | 6/2021 | Mazzardis |
| PP33,138 | P3 | 6/2021 | Mazzardis |
| PP33,384 | P3 | 8/2021 | Mazzardis |
| PP33,494 | P3 | 9/2021 | Mazzardis |
| PP33,635 | P2 | 11/2021 | Mazzardis |
| PP34,464 | P2 | 8/2022 | Mazzardis |
| PP34,465 | P2 | 8/2022 | Mazzardis |

OTHER PUBLICATIONS

Australia Plant Breeder Right Certificate No. 6480, App. No. 2017/316, Variety 'EB 12-3', Granted Jun. 11, 2021, 10 pgs.

*Primary Examiner* — Susan McCormick Ewoldt
(74) *Attorney, Agent, or Firm* — Randall Danskin, P.S.

(57) ABSTRACT

A new and distinct variety of blueberry plant, which is denominated varietally as 'NS 16-6' is described, with a very dense fruit cluster density, medium to long leaf length, large to very large fruit size, medium firm fruit, fruiting on one-year-old shoots only, medium plant vigor, and low to medium fruit acidity under the ecological conditions prevailing in Yanchep, Western Australia.

2 Drawing Sheets

Latin name: *Vaccinium* hybrid.

Variety denomination:

The invention relates to a new, novel, and distinct variety of blueberry plant, a *Vaccinium* hybrid, with a variety denomination hereinafter as 'NS 16-6'.

CROSS REFERENCE TO RELATED APPLICATIONS

This application claims the benefit of priority under 35 USC § 119 to Community Plant Variety Office (CPVO) Application No. 2022/0160 for Community Plant Variety Rights, filed on Jan. 18, 2022 for a blueberry plant with a variety denomination of 'NS16-6', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 16-6' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No.

28,334), and a pollen parent, blueberry plant 'EB 8-46' (U.S. Plant Pat. No. 26,173) during the 2013 growing season.

Prior Varieties. The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time, a medium fruit cluster density, and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-46, on the other hand, is characterized principally by an intermediate growth habit, a medium to strong vigor, an early season first pick date, and further produces very-large-sized, firm to very firm, high sweetness, and low acidity fruit under the ecological conditions occurring in Yanchep, Western Australia. Also, the pollen parent 'EB 8-46' exhibits an early date of bloom time and a November last pick date under the ecological conditions occurring in Yanchep, Western Australia. Further, the pollen parent 'EB 8-46' is semi-evergreen and produces fruit on one-year-old and current season's shoots.

Origin. The seed from the seed parent 'EB 9-4' produced approximately 2,400 plants following cross-pollination. These new plants were then grown at the aforementioned property, and fruit from these new plants was first observed in 2015. A subsequent assessment of these same self-fertile, new plants conducted during the 2016 growing season led to selecting the 'NS 16-6' variety for additional evaluation in 2017, which led to selection for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 16-6' variety was a distinct and new variety of blueberry plant found to be true to the original plant. The new variety of blueberry plant was considered to be novel in view of its very dense fruit cluster density, medium to long leaf length, large to very large fruit size, medium firm fruit, fruiting on one-year-old shoots only, medium plant vigor, and low to medium fruit acidity.

Comparisons. In comparison to the seed parent 'EB 9-4' under the ecological conditions occurring in Yanchep, Western Australia, the new variety is noteworthy. In this regard, the differences between and similarities of 'NS 16-6' and 'EB 9-4' are shown in Table 1.

In comparison to the pollen parent 'EB 8-46' under the ecological conditions occurring in Yanchep, Western Australia, the new variety is noteworthy. In this regard, the differences between and similarities of 'NS 16-6' and 'EB 8-46' are shown in Table 1.

The new variety of blueberry plant is readily distinguishable from the most closely related, known variety, the 'EB 8-46' blueberry plant (the pollen parent) described in U.S. Plant Pat. No. 26,173. In this regard, the differences between and similarities of 'NS 16-6' and 'EB 8-46' are shown in Table 1.

TABLE 1

Summary of Comparisons

| | 'NS 16-6' | 'EB 9-4' (Seed) | 'EB 8-46' (Pollen) |
|---|---|---|---|
| Fruit cluster density | Very dense | Medium | Medium to dense |
| Leaf length | Medium to long (59.9 mm) | Short to medium (67.47 mm) | Medium (62 mm) |
| Fruit size | Large to very large (20 × 14.39 mm) | Large to very large (24.52 × 14.20 mm) | Very large (21 mm) |
| Fruit firmness | Medium | Firm | Firm to very firm |
| Plant fruiting type | On one-year-old shoots only | On one-year-old and current season's shoots | On one-year-old and current season's shoots |
| Plant vigor | Medium | Medium | Medium to strong |
| Fruit acidity | Low to medium | Low to medium | Low |
| Year observations were taken | 2nd year of growth | 3rd year of growth | 6th fruiting season |

In addition, Table 2 below compares the 'NS 16-6' variety to sibling cultivars that resulted from the same seed parent 'EB 9-4' and pollen parent 'EB 8-46', namely, 'NS 15-5' (U.S. Plant Pat. No. 33,154), 'NS 15-13' (U.S. Plant Pat. No. 33,138), 'NS 15-22' (U.S. Plant Pat. No. 33,384), and 'NS 16-15' (U.S. Plant Pat. No. 33,112).

TABLE 2

Comparison to Sibling Cultivars

| | 'NS 16-6' | 'NS 15-5' | 'NS 15-13' |
|---|---|---|---|
| Fruit cluster density | Very dense | Medium to dense | Sparse to medium |
| Leaf Length | Medium to long (59.9 mm) | Medium to long (60.7 mm) | Medium (56.9 mm) |
| Fruit size | Large to very large (20 × 14.39 mm) | Large to very large (20 × 13.53 mm) | Large (19 × 13.99 mm) |
| Fruit firmness | Medium | Medium | Medium to firm |
| Plant fruiting type | On one-year-old shoots only | On one-year-old and current season's shoots | On one-year-old shoots only |
| Plant vigor | Medium | Strong | Medium to strong |
| Fruit acidity | Low to medium | Very low to low | Low to medium |
| Fruit sweetness | Medium | Medium | Medium |
| Vegetative bud burst timing | Early, end of June | Early, end of May | Early, end of May |
| Year observations were taken | 2nd year of growth | 3rd year of growth | 3rd year of growth |

| | 'NS 15-22' | 'NS 16-15' |
|---|---|---|
| Fruit cluster density | Medium | Dense |
| Leaf Length | Medium to long (58.4 mm) | Medium (57.0 mm) |
| Fruit size | Large to very large (21 × 14.59 mm) | Large (19 × 13.05 mm) |

TABLE 2-continued

| Comparison to Sibling Cultivars | | |
|---|---|---|
| Fruit firmness | Medium | Firm |
| Plant fruiting type | On one-year-old shoots only | On one-year-old shoots only |
| Plant vigor | Strong | Medium to strong |
| Fruit acidity | Low | Low |
| Fruit sweetness | Medium | Medium |
| Vegetative bud burst timing | Early, end of May | Early, mid-June |
| Year observations were taken | 3rd year of growth | 2nd year of growth |

BRIEF DESCRIPTION OF THE DRAWINGS

The accompanying drawings are color photographs of the new blueberry plant 'NS 16-6' during the second year of growth under the ecological conditions prevailing at the breeder's property, which is located at Yanchep Springs in Yanchep, Western Australia.

Figure 1:
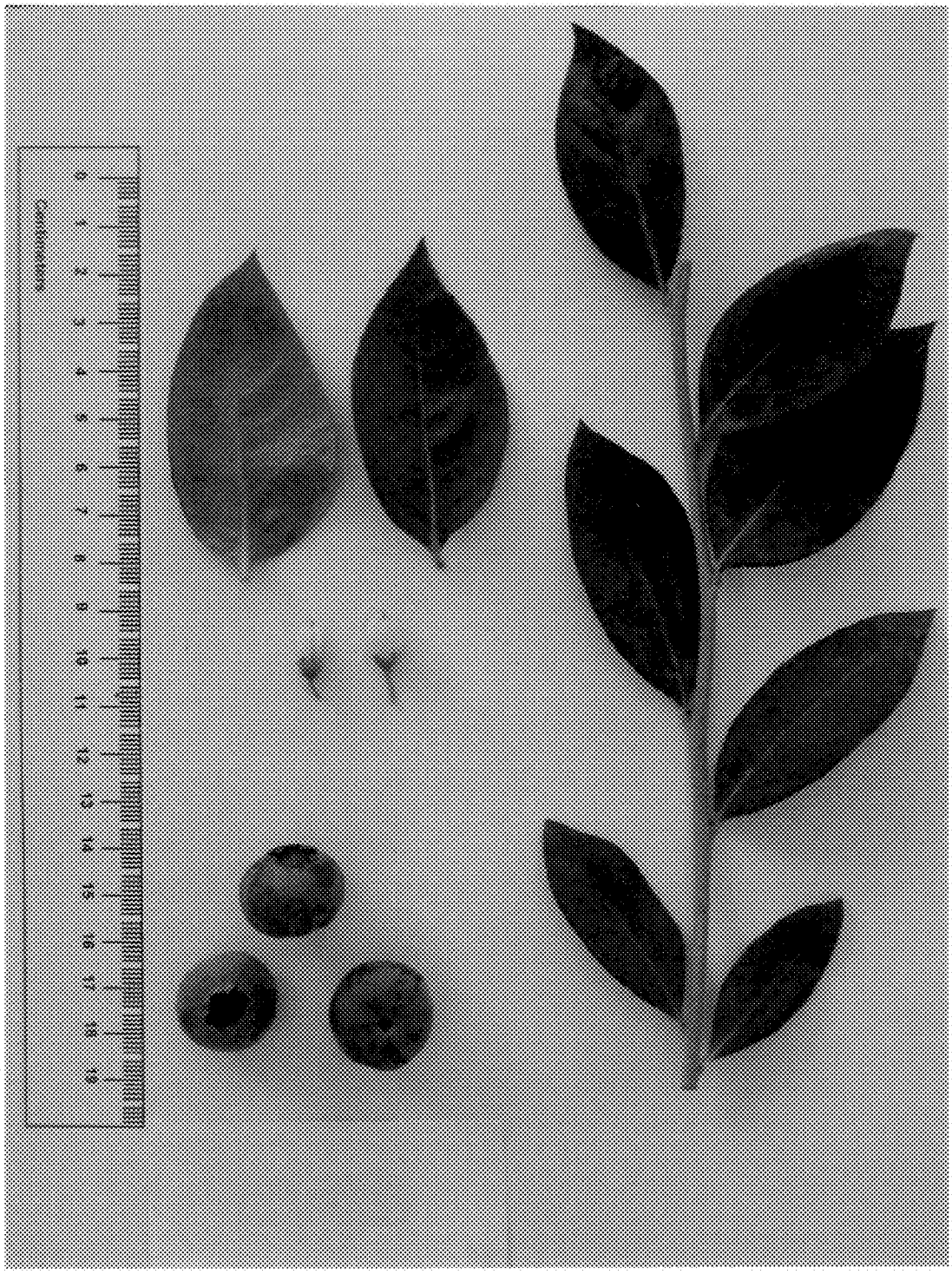
FIG. 1 is a color photograph, which shows fruit, blooms, leaves, and a portion of a vegetative stem of the new blueberry plant 'NS 16-6', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
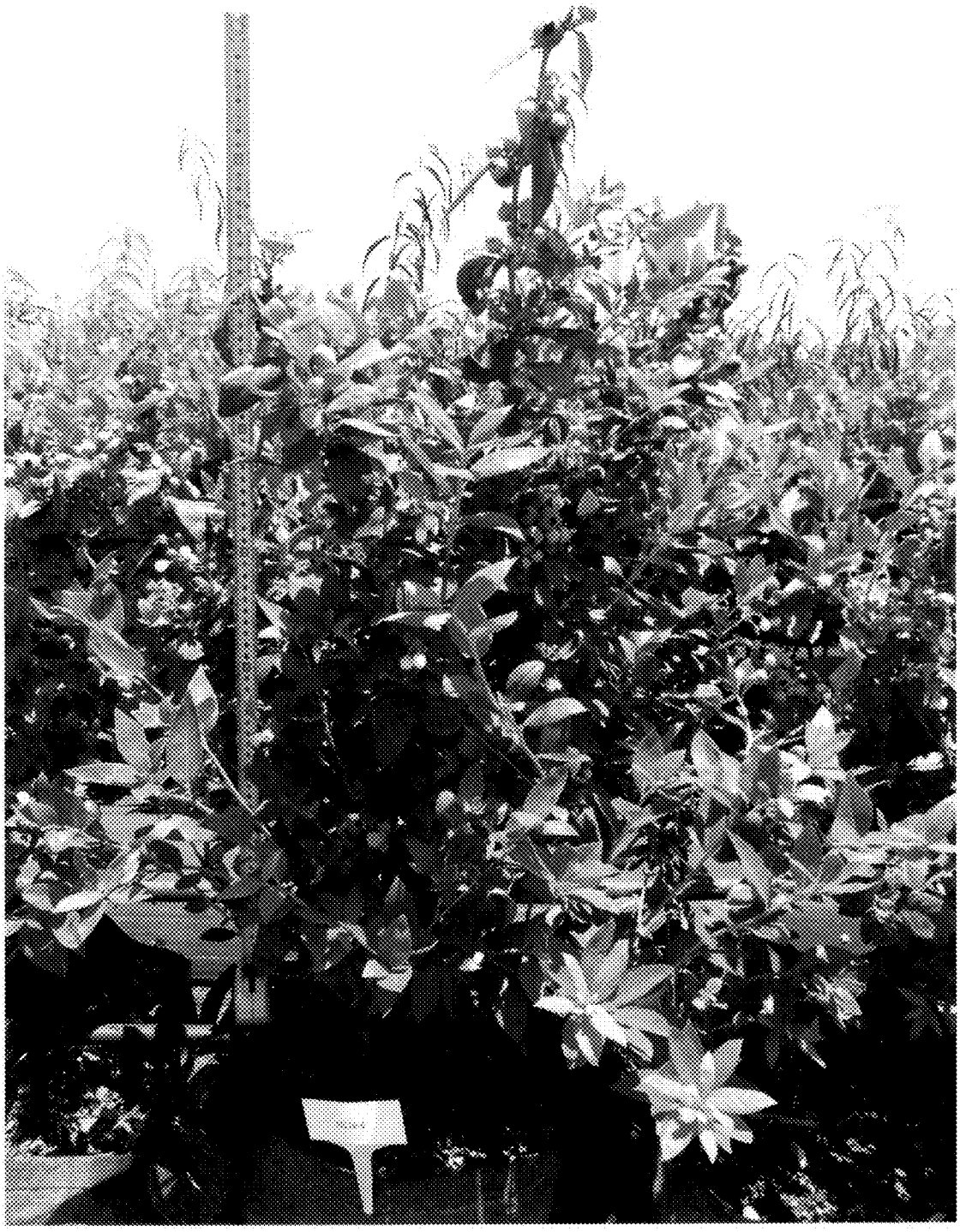
FIG. 2 is a color photograph, which shows the new blueberry plant 'NS 16-6.' This photograph depicts a mature bush with ripe and unripe fruits, the fruit size, and the semi-upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the second year of growth under the ecological conditions prevailing at the breeder's property, which is located at Yanchep Springs in Yanchep, Western Australia.

Plant: General.

*Vigor*.—Considered medium for the species, in like manner to the commercial variety 'DrisBlueSeven' (U.S. Plant Pat. No. 24,605).

*Growth habit*.—Considered semi-upright, in like manner to the commercial varieties 'Bluetta' (unpatented) and 'Draper' (U.S. Plant Pat. No. 15,103).

*Average size of plant*.—0.85 meters in height by 0.57 meters in width.

*Internode length* (*space between nodes*).—Considered medium, 19.9 millimeters (mm).

*Bark color*.—RHS Reddish Brown Group 177B.

*Color, one year old shoots*.—RHS Light Yellow Green 144D, also considered "green" in like color to the commercial variety 'Puru' (U.S. Plant Pat. No. 6,701).

*Fruiting type*.—On one-year-old shoots only, in like manner to the commercial varieties 'Darrow' (unpatented) and 'Patriot' (unpatented).

Foliage: General.

*Average leaf length*.—Considered medium to long for the species, 59.9 mm.

*Average leaf width*.—Considered medium for the species, 23.1 mm.

*Color of leaf upper*.—RHS Greyish Olive Green Group NN137B.

*Color of leaf underside*.—RHS Pale Green Group N138C.

*Vein color of plant leaf*.—RHS Moderate Yellow Green Group 139D.

*Venation pattern of leaf*.—Pinnate reticulate.

*Leaf apex texture*.—Glabrous.

*Leaf apex shape*.—Acute.

*Leaf base shape*.—Acute.

*Leaf shape*.—Elliptic.

*Leaf margin*.—Entire.

*Leaf arrangement of plant*.—Alternate.

*Petiole length*.—3.63 mm.

*Petiole diameter*.—1.75 mm.

*Petiole color*.—RHS Strong Yellow Green 145A.

Flowers:

*Number of flowers/inflorescence*.—8 to 10.

*Length of inflorescence* (*excluding pedicel*).—Considered medium, 4.53 mm.

*Infructescence density*.—Considered medium, in like manner to the commercial variety 'Toro' (unpatented).

*Corolla shape*.—Urceolate.

*Corolla tube surface texture*.—Ridges are present on the corolla tube.

*Average corolla length*.—12.3 mm.

*Corolla diameter*.—7.57 mm.

*Corolla aperture size*.—3.76 mm.

*Corolla color*.—RHS White Group NN155B.

*Pedicel color*.—RHS Light Yellow Green Group 145B.

*Pedicel length*.—7.03 mm.

*Average calyx diameter*.—Considered small, 4.02 mm.

*Average calyx basin depth*.—Considered shallow, 1.14 mm.

*Attitude of sepals*.—Erect.

*Type of sepals*.—Straight.

Reproductive organs:

*Size of pollen anthers.*—3.36 mm.

*Color of pollen anthers.*—RHS Brownish Orange Group N167B.

*Pistil length.*—10 mm.

*Pistil color.*—RHS Light Yellow Green Group 145D.

Fruit:

*Color of unripe fruit.*—RHS Strong Yellow Green Group N144C.

*Color of fruit skin.*—RHS Bluish Black Group 203C, also considered "dark blue" in like color to the commercial variety 'Heerma' (unpatented), at time of bloom removal.

*Color of ripe fruit flesh.*—RHS Light Yellow Green Group 145C.

*Color of seeds.*—RHS Brownish Orange Group 172C.

*Average fruit size.*—Large to very large, 20 mm in diameter and 14.39 mm in height.

*Average weight of fruit.*—3.3 grams.

*Berry shape.*—Considered oblate.

*Sweetness when ripe.*—Considered medium for the species.

*Firmness when ripe.*—Considered medium for the species.

*Acidity when ripe.*—Considered low for the species.

*Cluster density.*—Considered very dense for the species.

*Average fruit production.*—2.5 kilograms on a two-year-old bush.

*Storability of fruit.*—Considered excellent for the species.

*Market use of fruit.*—1st grade fresh market fruit.

*Date of bud burst.*—This variety is evergreen under the ecological conditions prevailing in Yanchep, Western Australia, but a bud break occurs at the end of June, which is considered early in timing.

*Date of bloom time on 1-year-old shoots.*—This variety is evergreen under the ecological conditions prevailing in Yanchep, Western Australia, but a bloom time occurs at the end of July, which is considered early, in like manner to the commercial variety 'Weymouth' (unpatented).

*Duration of bloom time and bloom intensity.*—4 weeks; bloom intensity is considered strong.

*Beginning of fruit ripening.*—Considered early on one-year-old shoot, in like manner to the commercial variety 'Blueray' (unpatented).

*First pick date.*—The observed date of the first pick is approximately October under the ecological conditions prevailing in Yanchep, Western Australia.

*Last pick date.*—The observed date of the last pick is approximately November under the ecological conditions prevailing in Yanchep, Western Australia.

*Pollination requirements.*—Self-fertile.

*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant named 'NS 16-6', substantially as illustrated and described, which is characterized principally as to novelty by a very dense fruit cluster density, medium to long leaf length, large to very large fruit size, medium firm fruit, fruiting on one-year-old shoots only, medium plant vigor, and low to medium fruit acidity under the ecological conditions prevailing in Yanchep, Western Australia.

* * * * *